US012257377B1

(12) United States Patent
Rayhanabad

(10) Patent No.: US 12,257,377 B1
(45) Date of Patent: *Mar. 25, 2025

(54) METHOD OF PERFORMING A MINIMALLY INVASIVE BYPASS

(71) Applicant: Simon B. Rayhanabad, Huntington Beach, CA (US)

(72) Inventor: Simon B. Rayhanabad, Huntington Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/587,878

(22) Filed: Feb. 26, 2024

Related U.S. Application Data

(60) Continuation-in-part of application No. 17/574,452, filed on Jan. 12, 2022, which is a division of
(Continued)

(51) Int. Cl.
*A61F 2/07* (2013.01)
*A61M 1/36* (2006.01)
(Continued)

(52) U.S. Cl.
CPC ............. *A61M 1/3655* (2013.01); *A61F 2/07* (2013.01); *A61B 2017/00252* (2013.01); *A61B 2017/00557* (2013.01); *A61B 2017/00778* (2013.01); *A61B 2017/1107* (2013.01); *A61F 2002/061* (2013.01); *A61F 2002/065* (2013.01); *A61F 2002/075* (2013.01); *A61F 2002/077* (2013.01); *A61F 2210/0014* (2013.01); *A61F 2220/0075* (2013.01); *A61F 2250/0003* (2013.01);
(Continued)

(58) Field of Classification Search
CPC . A61B 2017/00252; A61B 2017/00778; A61F 2002/065; A61F 2/07; A61F 2/064; A61M 27/002
See application file for complete search history.

(56) References Cited

U.S. PATENT DOCUMENTS

| 6,035,856 A * | 3/2000 | LaFontaine | A61F 2/064 623/1.11 |
| 11,534,286 B1 * | 12/2022 | Rayhanabad | A61F 2/064 623/1.13 |
| 2008/0195125 A1 * | 8/2008 | Hoffman | A61B 17/11 606/153 |

FOREIGN PATENT DOCUMENTS

| JP | 2008502453 A | * | 1/2008 | |
| WO | WO-0057817 A1 | * | 10/2000 | A61F 2/06 |
| WO | WO-0115618 A2 | * | 3/2001 | A61B 17/11 |

(Continued)

OTHER PUBLICATIONS

JP2008502453 translation (Year: 2008).*

*Primary Examiner* — Brian E Pellegrino
(74) *Attorney, Agent, or Firm* — Steven R. Vosen

(57) ABSTRACT

A method is disclosed for performing a medical procedure on a patient with two blood vessels, including a first lumen and a second lumen. The method involves making an incision in the skin to access the first and second locations of the blood vessels, puncturing the blood vessels at these locations, and inserting stent-grafts into the lumens. The stent-grafts include branching vascular grafts that are expanded to contact the inner surfaces of the lumens. The first and second vascular grafts are then connected to each other, providing fluid communication between the blood vessels. The incision is then closed, leaving the stent-grafts beneath the patient's skin. The method may be used for bypass procedures or arteriovenous grafts, among others.

6 Claims, 6 Drawing Sheets

Related U.S. Application Data application No. 17/399,811, filed on Aug. 11, 2021, now Pat. No. 11,534,286.

(60) Provisional application No. 63/614,844, filed on Dec. 26, 2023, provisional application No. 63/064,320, filed on Aug. 11, 2020.

(51) Int. Cl.
 *A61B 17/00* (2006.01)
 *A61B 17/11* (2006.01)
 *A61F 2/06* (2013.01)
 *A61M 27/00* (2006.01)

(52) U.S. Cl.
 CPC .... *A61F 2250/0069* (2013.01); *A61M 27/002* (2013.01); *Y10S 623/903* (2013.01)

(56) References Cited

FOREIGN PATENT DOCUMENTS

| | | | | |
|---|---|---|---|---|
| WO | WO-0178801 A2 | * | 10/2001 | ............. A61B 17/11 |
| WO | WO-2015190928 A1 | * | 12/2015 | ............. A61F 2/064 |

* cited by examiner

METHOD OF PERFORMING A MINIMALLY INVASIVE BYPASS

CROSS-REFERENCE TO RELATED APPLICATIONS

This application is a continuation-in-part of U.S. patent application Ser. No. 17/574,452, filed Jan. 12, 2022, which is a divisional of U.S. patent application Ser. No. 17/399,811, filed on Aug. 11, 2021, which issued on Dec. 27, 2022 as U.S. Pat. No. 11,534,286, and which claimed the benefit of U.S. Provisional Application No. 63/064,320, file on Aug. 11, 2020. This application also claims the benefit of U.S. Provisional Application No. 63/614,844 filed Dec. 25, 2023. The contents of each of the applications and patents in this paragraph are hereby incorporated by reference in their entirety.

BACKGROUND OF THE INVENTION

Field of the Invention

The present invention relates generally to medical procedures, and more particularly to minimally invasive procedures to provide a bypass or arteriovenous graft to a patient.

Discussion of the Background

There are a variety of surgical procedures, such as those that require access to the aorta, or vena cava, which requires a surgeon to access these blood vessels through the abdomen or the chest. Thus, for example, coronary bypass surgery, in which blood flow is redirected around a section of a blocked or partially blocked artery, is performed by making a long incision in the chest, cutting the center of the chest along the breastbone, spreading the rib cage open to expose the heart, and inserting a healthy blood vessel, often from inside the chest wall or from the lower leg by attaching the ends above and below the blocked artery so that blood flow is redirected around the narrowed part of the diseased artery. Such procedures are highly invasive.

On the other hand, there are several procedures that access the heart, but which are much less invasive, such as coronary stent placement. This procedure is performed with a stent delivery apparatus in which a compressed, self-expanding stent is placed in the tip at a distal end of a delivery system. The tip is then inserted into an artery in the groin, arm or wrist area and is directed through the artery and towards the heart. Once the tip reaches the required location, the delivery system is actuated, releasing the compressed stent in the artery, which then expands to sit against the inner walls of the artery near the heart, and the delivery system is removed.

Unfortunately, devices used for such non-invasive procedures are not useful for performing more complicated procedures, such as coronary bypass surgery.

There is a need in the art for less invasive surgical procedures and for medical devices that support such procedures. In addition, to coronary bypass procedures, such devices should also be useful in procedures that involve other large blood vessels, such as the vena cava, iliac, or common femoral artery or providing an arteriovenous graft to a patient.

BRIEF SUMMARY OF THE INVENTION

The present invention overcomes the disadvantages of prior art by providing an endovascular stent-graft having an extravascular extension, also referred to herein, without limitation, as an "stent-graft with branching graft." The use of the endovascular stent-graft is described, without limitation, as being delivered into a blood vessel.

Certain aspects provide a minimally invasive bypass procedure, such as a carotid-carotid bypass, a carotid-subclavian bypass, a carotid-axillary bypass, an axillo-femoral bypass, an aortofemoral bypass, an iliac-femoral bypass, an iliac-popliteal bypass, or an femoral-popliteal bypass. Other aspects include a procedure where blood vessels are accessed by an incision in a patent's back.

Certain other aspects provide a minimally invasive arteriovenous graft procedure, such as an aorta-vena cava graft, an iliac-iliac arteriovenous graft, or a vena cava-femoral arteriovenous graft.

One aspect provides a method of performing a procedure on a patient having a first blood vessel including a first lumen having a first lumen inner surface and a second blood vessel including a second lumen with a second lumen inner surface. The method includes: incising a skin of the patient to form an incision, where the incision is positioned to provide access a first location of the first blood vessel and to provide access to a second location of the second blood vessel; puncturing the first blood vessel at the first location to form a first puncture; puncturing the second vessel blood at the second location to form a second puncture; providing a first stent-graft of a first endovascular stent-graft through the incision and the first puncture and into the first lumen to contact the first lumen inner surface, where the first endovascular stent-graft includes a branching first vascular graft having a first vascular graft end; connecting the first vascular graft end to the second puncture; and closing the incision. The method is such that the first endovascular stent-graft is below the skin of the patient and such that fluid communication is provided between the first blood vessel at the first puncture and the second blood vessel at the second puncture.

In one aspect, connecting the first vascular graft end and the second puncture includes performing an anastomosis between the first vascular graft end and the second blood vessel at the second puncture.

In another aspect, the method further includes: providing a second stent-graft of a second endovascular stent-graft through the incision and the second puncture and into the second lumen to contact the second lumen inner surface, where the second endovascular stent-graft includes a branching second vascular graft having a second vascular graft end; where the connecting the first vascular graft end to the second puncture includes connecting the first vascular graft end to the second vascular graft end, and such that the second endovascular stent-graft is below the skin of the patient.

Yet other aspects provide a method where the incising includes a first incising to form a first incision and a second incising to form a second incision, where the first incision is positioned to provide access to the first location and were the second incision is positioned to provide access to the second location, where the connecting the first vascular graft end to the second puncture includes subcutaneously threading the first vascular graft end towards second puncture and forming an anastomosis between the first vascular graft end and the second blood vessel at the second puncture.

In yet other aspects, the incision includes a first incision and a second incision, where the first incision is positioned to provide access to the first location and were the second incision is positioned to provide access to the second location, and the method further includes providing a second stent-graft of a second endovascular stent-graft through the incision and the second puncture and into the second lumen to contact the second lumen inner surface, where the second endovascular stent-graft includes a branching second vascular graft having a second vascular graft end, where the connecting the first vascular graft end to the second puncture includes connecting the first vascular graft end to the second vascular graft end, where the closing the incision includes closing the first incision and closing the second incision, and such that the second endovascular stent-graft is below the skin of the patient.

Certain other aspects further provide incising the skin to form a third incision; connecting the first vascular graft end to the second vascular graft end through the third incision; and closing the third incision.

Certain aspects provide a method of performing a procedure on a patient having a first blood vessel including a first lumen having a first lumen inner surface and a second blood vessel including a second lumen with a second lumen inner surface. The method includes: incising a skin of the patient to form a first incision, where the first incision is positioned to provide access a first location of the first blood vessel; incising a skin of the patient to form a second incision, where the second incision is positioned to provide access a second location of the second blood vessel; puncturing the first blood vessel at the first location to form a first puncture; puncturing the second vessel blood at the second location to form a second puncture; providing a first stent-graft of a first endovascular stent-graft through the first incision and the first puncture to contact the first lumen inner surface, where the first endovascular stent-graft includes a branching first vascular graft having a first vascular graft end; providing a second stent-graft of a second endovascular stent-graft through the second incision and the second puncture to contact the second lumen inner surface, where the second endovascular stent-graft includes a branching second vascular graft having a second vascular graft end; subcutaneously threading the first vascular graft end towards the second vascular graft end; connecting the first vascular graft end to the second vascular graft end; closing the first incision; and closing the second incision, such that the first endovascular stent-graft and second endovascular stent-graft are below the skin of the patient and such that fluid communication is provided between the first blood vessel at the first puncture and the second blood vessel at the second puncture.

These features together with the various ancillary provisions and features which will become apparent to those skilled in the art from the following detailed description, are attained by the endovascular stent-graft with an extravascular extension and method of the present invention, preferred embodiments thereof being shown with reference to the accompanying drawings, by way of example only, wherein:

BRIEF DESCRIPTION OF THE SEVERAL
VIEWS OF THE DRAWING

Reference symbols are used in the Figures to indicate certain components, aspects or features shown therein, with reference symbols common to more than one Figure indicating like components, aspects or features shown therein.

DETAILED DESCRIPTION OF THE
INVENTION

The following description includes the disclosure of an endovascular stent-graft and several minimally invasive interventions enabled by the endovascular stent-graft. In general, as described subsequently, the endovascular stent-graft includes a stent-graft and a vascular graft that branches from the stent-graft and forms an extravascular extension. The endovascular stent-graft with an extravascular extension may be inserted into the body near, for example, the aorta, iliac, or femoral areas, and through an incision in a target blood vessel, such as an artery or vein, and with the graft extending through the incision to the outside of the target blood vessel. The graft then provides access to the circulatory system.

Figure 1:
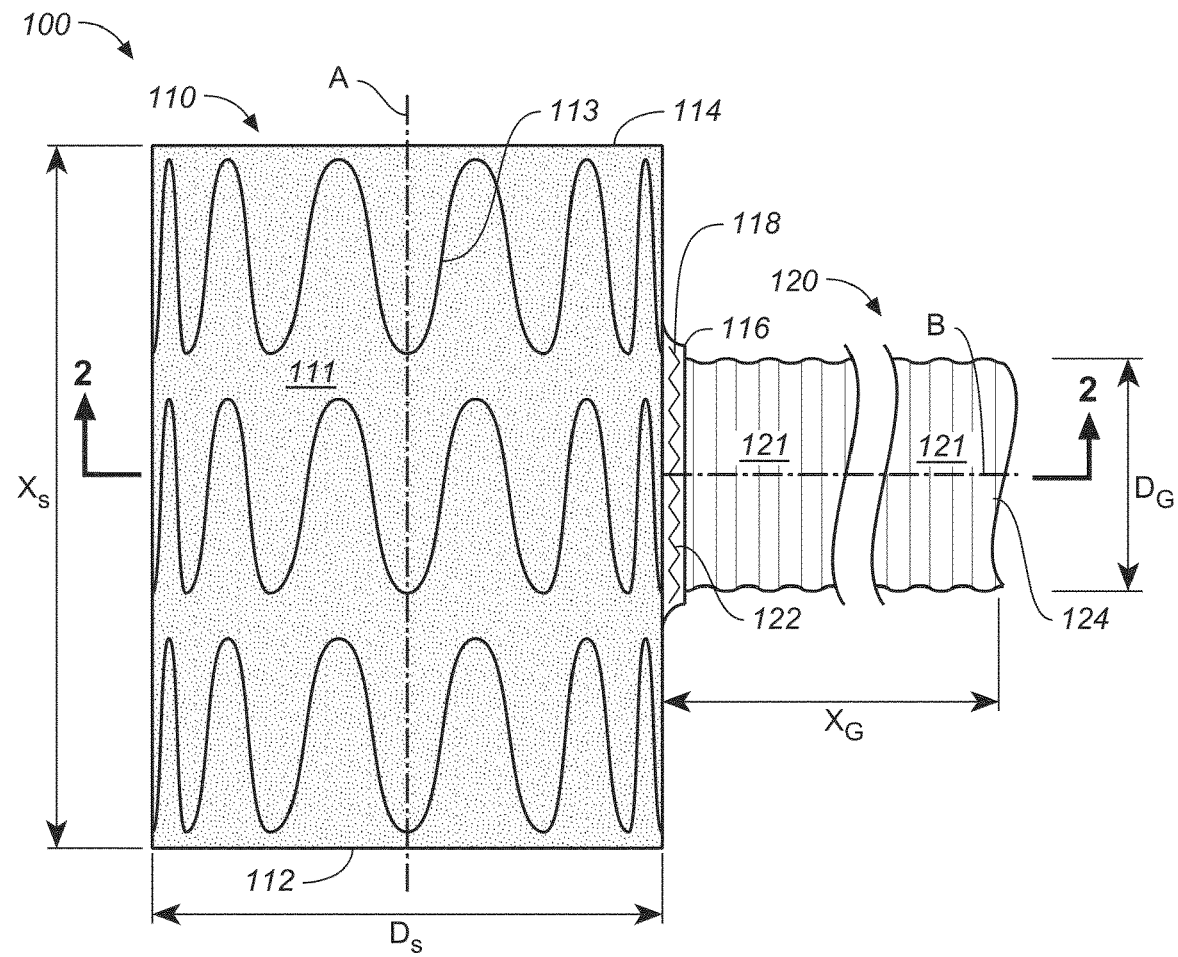
FIG. 1 is a side view of a first embodiment endovascular stent-graft.
Figure 2:
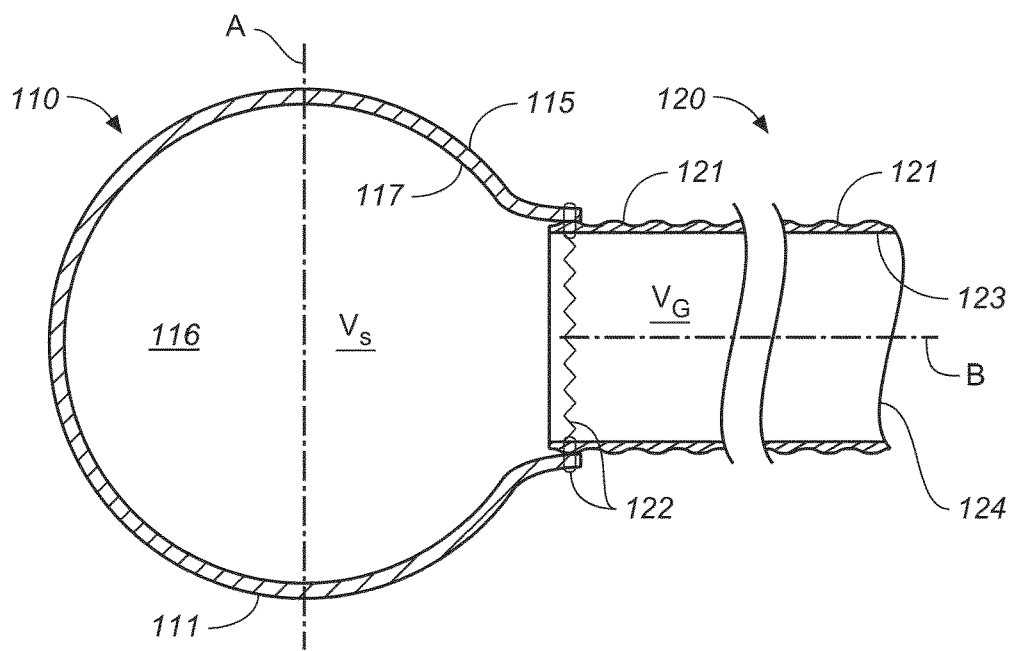
FIG. 2 is a sectional top view 2-2 of FIG. 1.

FIG. 1 is a side view of a first embodiment endovascular stent-graft 100 and FIG. 2 is a sectional top view 2-2 of FIG. 1. Endovascular stent-graft 100 includes a stent-graft 110 and a vascular graft 120 that branches from the stent-graft.

Stent-graft 110 has an outer surface 115 and an inner surface 117 and includes a stent 113, which is a metal framework or mesh, covered by a graft 111, which is a thin fabric formed from a polyester, such as expanded polytetrafluoroethylene (ePTFE). Stent 113 is a collapsible and self-expanding structure formed from a metal alloy such as nickel titanium, which also known as nitinol, and graft 111 of the stent-graft is a barrier to the flow fluids, such as blood.

The expanded shape of stent-graft 110 is generally cylindrical, with a centerline A, a diameter Ds, and a length, Xs, between a first end 112 and a second end 114, and a lumen Vs. Stent-graft 110 differs from commercially available stent-grafts in that it includes an aperture 116. As discussed subsequently, the shape of aperture 116 matches that vascular graft 120. In certain embodiments, aperture 116 is located midway between first end 112 and second end 114, as shown in the Figures. In certain other embodiments, aperture 116 is closer to one of first end 112 or second end 114.

Vascular graft 120 has an outer surface 121 and an inner surface 123 and is generally cylindrical and extends from a first end 122 to a second end 124. The material of vascular graft 120 may be, for example and without limitation, formed from ePTFE or may be a metal framework or mesh similar to the material of stent-graft 110. Vascular graft 120 is generally cylindrical in shape, with a centerline B, diameter Dg, and a length, Lg, between first end 122 and second end 124, and a lumen VG.

First end 112 of vascular graft 120 extends from aperture 116, such that a lumen of the endovascular stent-graft 100 includes a lumen of the stent-graft 110 and a lumen of the vascular graft 120. In one embodiment, first end 112 is joined to aperture 116 of stent-graft 110 by a suture 118, which may be a conventional medical suture. In other embodiments, stent-graft 110 and vascular graft 120 are joined by bonding, such as by an adhesive, or are formed as a single piece in the manufacturing process.

In certain embodiments, it is preferred that the portion of sent-graft 110 near aperture 116 includes a sufficient amount of stent 113 material so as to provide an outwards radial force so that the stent-graft maintains the circular shape of the aperture.

In certain embodiments, the diameter of stent-graft 110, Ds, is from 1 cm to 5 cm, the length of the stent-graft, Ls, is from 15 cm to 40 cm. Typically, the diameter Ds is selected to be slightly larger than the target blood vessel into which is to be inserted. The diameter of vascular graft 120, Dg, is from 5 cm to 10 cm, and the length of vascular graft 120, Lg, is from 3 cm to 70 cm.

By way of example, a commercially available stent-graft which is similar to stent-graft 110 is, without limitation, a GORE® VIABAHN® VBX Balloon Expandable Endoprosthesis (see https://www.goremedical.com/products/vbx), manufactured by W. L. Gore & Associates, Inc. (Newark, Delaware). Further, by way of example, a commercially available grafts which is similar to vascular graft 120 is, without limitation, an expandable stent-graft similar to that of stent-graft 110 or is a GORE-TEX© Stretch Vascular Graft (see https://www.goremedical.com/products/vg-stretch), manufactured by W. L. Gore & Associates, Inc. (Newark, Delaware).

Figure 4:
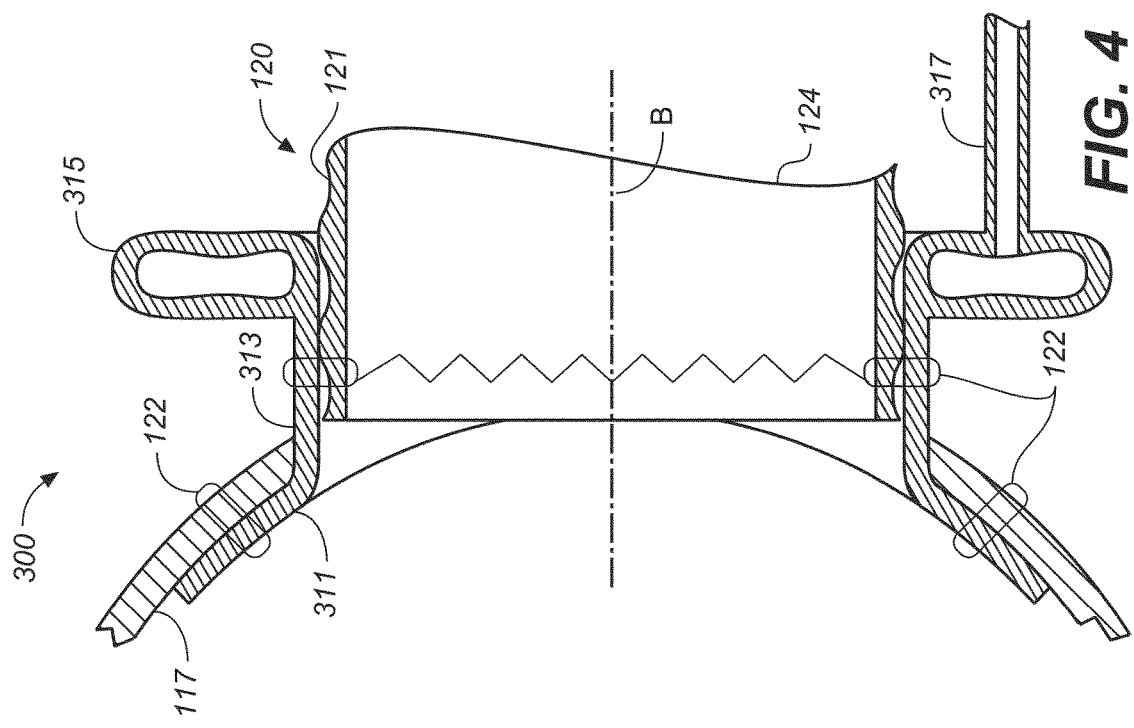
FIG. 4 is a sectional top view 3-3 of FIG. 3.
Figure 3:
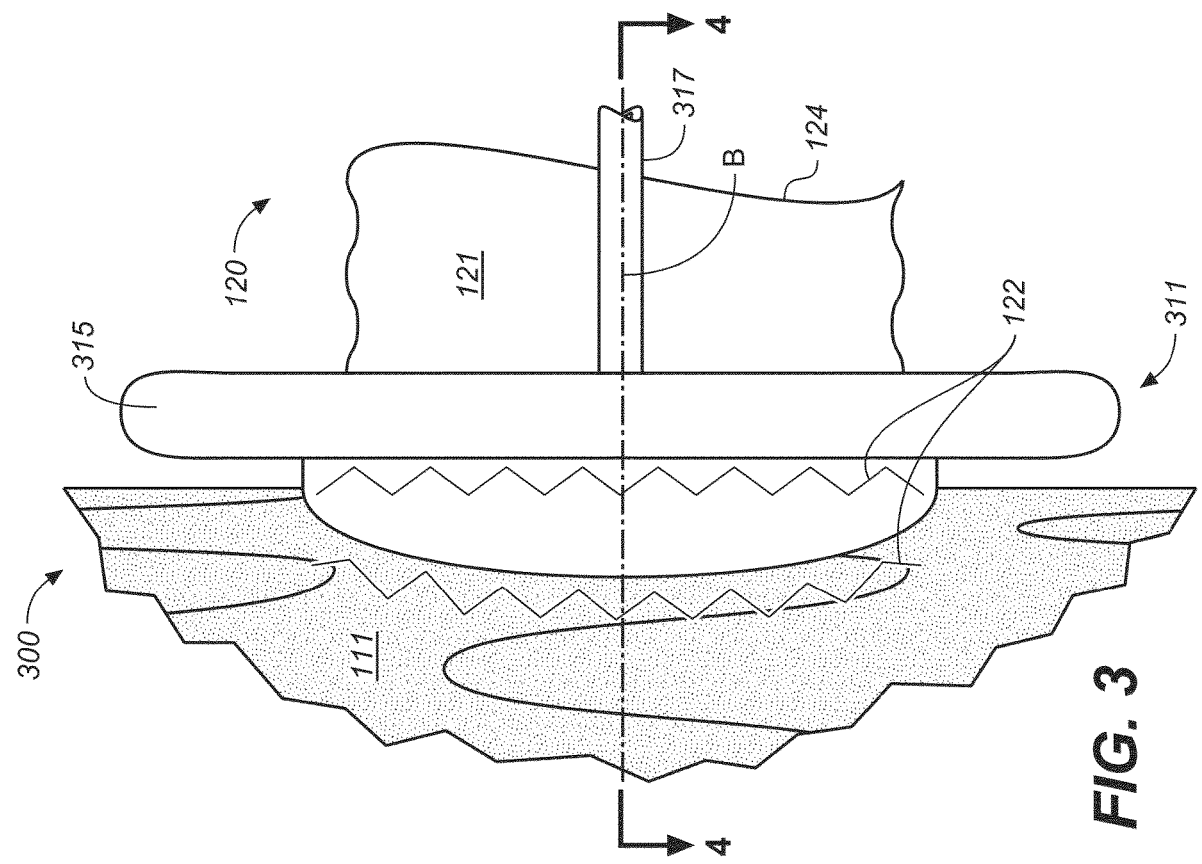
FIG. 3 is a side view of a portion of a second embodiment endovascular stent-graft.

FIG. 3 is a detailed side view of a second embodiment endovascular stent-graft 300 and FIG. 4 is a sectional top view 4-4 of FIG. 3. Endovascular stent-graft 300 is generally similar to endovascular stent-graft 100, except as explicitly noted.

Endovascular stent-graft 300 includes stent-graft 110 and vascular graft 120, as discussed above, and also includes a first portion 311 attached to inner surface 117 of stent-graft 110, a second portion 313 attached to inner surface 123 of vascular graft 120, a balloon 315, and a tube 317 in fluid communication with the balloon and which is used for inflating/deflating the balloon. An end of tube 317 that is not attached to balloon 315 may be attached to a pump and/or a sealing mechanism to maintain inflation of the balloon. First portion 311 and inner surface 117, and second portion 313 and inner surface 123 are attached, for example and without limitation, with suture 118. Alternatively, one or both of these attachments may be manufactured as one piece. Balloon 315 may be inflated using tube 317 to force the balloon is against graft 111.

Figure 7:
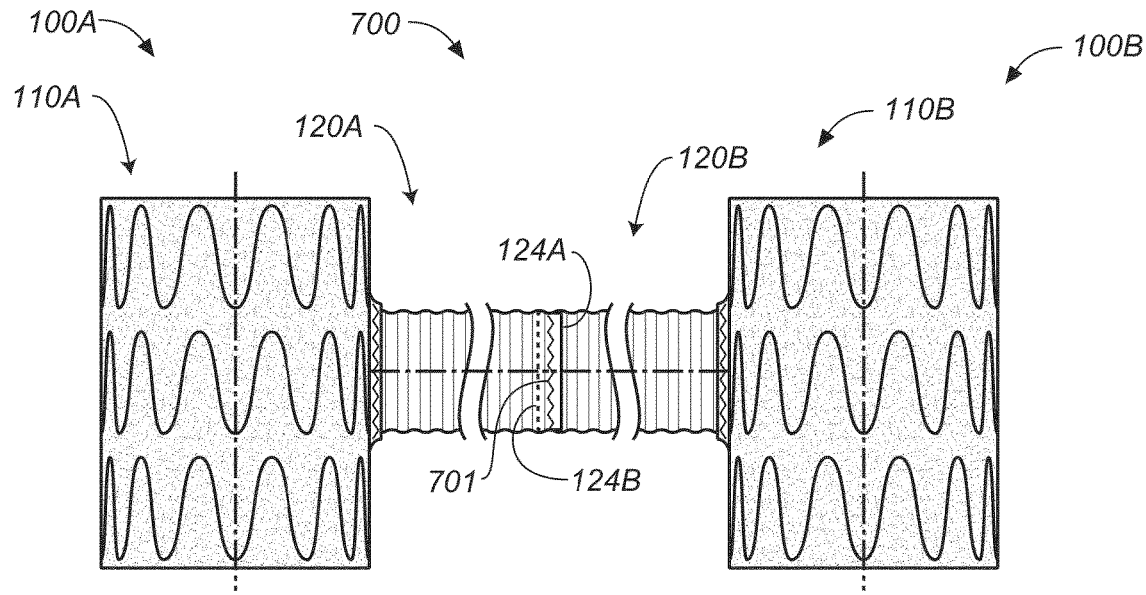
FIG. 7 is a side view of a second embodiment endovascular stent-graft utilizing two stent-grafts of FIG. 1.
Figure 8:
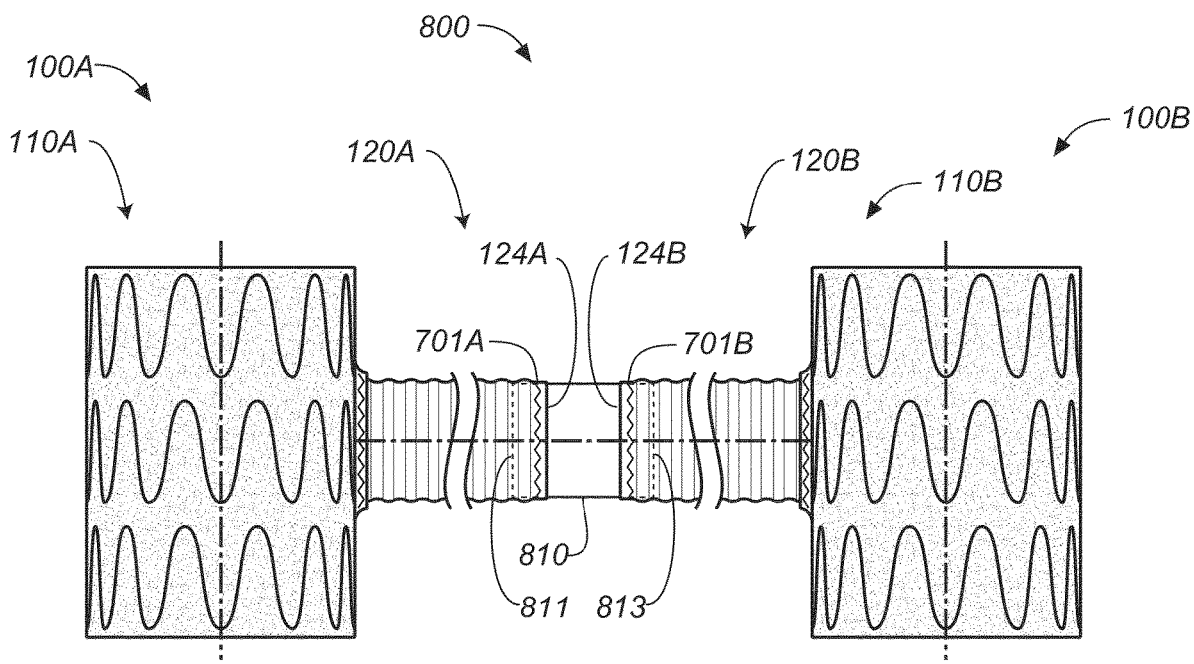
FIG. 8 is a side view of a third embodiment endovascular stent-graft utilizing two stent-grafts of FIG. 1.

In certain embodiments, two endovascular stent-grafts, which may be endovascular stent-graft 100, endovascular stent-graft 300 or a combination thereof, are joined at their respective second end 124 to form a "dual endovascular stent-graft" that provides fluid communication the stent-graft 110 of each endovascular stent-graft. Thus, for example, FIG. 7 is a side view of a first embodiment dual endovascular stent-graft 700 and FIG. 8 is a side view of a second embodiment dual endovascular stent-graft 800. Dual endovascular stent-graft 700 and dual endovascular stent-graft 800 are shown, without limitation, as showing the joining of two endovascular stent-graft 100, such as first endovascular stent-graft 100A and second endovascular stent-graft 100B.

Dual endovascular stent-graft 700 includes first endovascular stent-graft 100A having a first stent-graft 110A and a first vascular graft 120A with a first end 124A and second endovascular stent-graft 100B having a second stent-graft 110B and a second vascular graft 120B with a second end 124B. First endovascular stent-graft 100A and second endovascular stent-graft 100B are joined by inserting second end 124B into first vascular graft 120A and stitching a suture 701, which is generally similar to a suture 118, to join first vascular graft 120A and second vascular graft 120B. Alternatively other methods of joining first vascular graft 120A and second vascular graft 120B, such as an adhesive, may be used.

Dual endovascular stent-graft 800 is generally similar to dual endovascular stent-graft 700 except as explicitly stated. Dual endovascular stent-graft 800 includes a tube 810 having a first end 811 and a second end 813, and a pair of sutures 701 shown as a first suture 701A and a second suture 701B. Tube 810 is formed of a biocompatible material and may, for example and without limitation, be generally similar to vascular graft 120. First endovascular stent-graft 100A and second endovascular stent-graft 100B are joined by: 1) inserting first end 811 into first vascular graft 120A and stitching with first suture 701A; 2) inserting second end 813 into second vascular graft 120B and stitching with suture 701B. Alternatively other methods of joining first vascular graft 120A and second vascular graft 120B to joining tube 810, such as an adhesive, may be used.

Uses of the Inventive Endovacular Stent-Graft

The endovascular stent-grafts described above may be used for any one of a number of procedures the require access to the circulatory system.

A first use of endovascular stent-graft 100 or 300 is to provide access to a body, such as, but are not limited to, accessing the heart to perform a heart valve repair procedure, or to provide access to the aorta for any intra-aortic procedure on a blocked lower part of the aorta.

Figure 6:
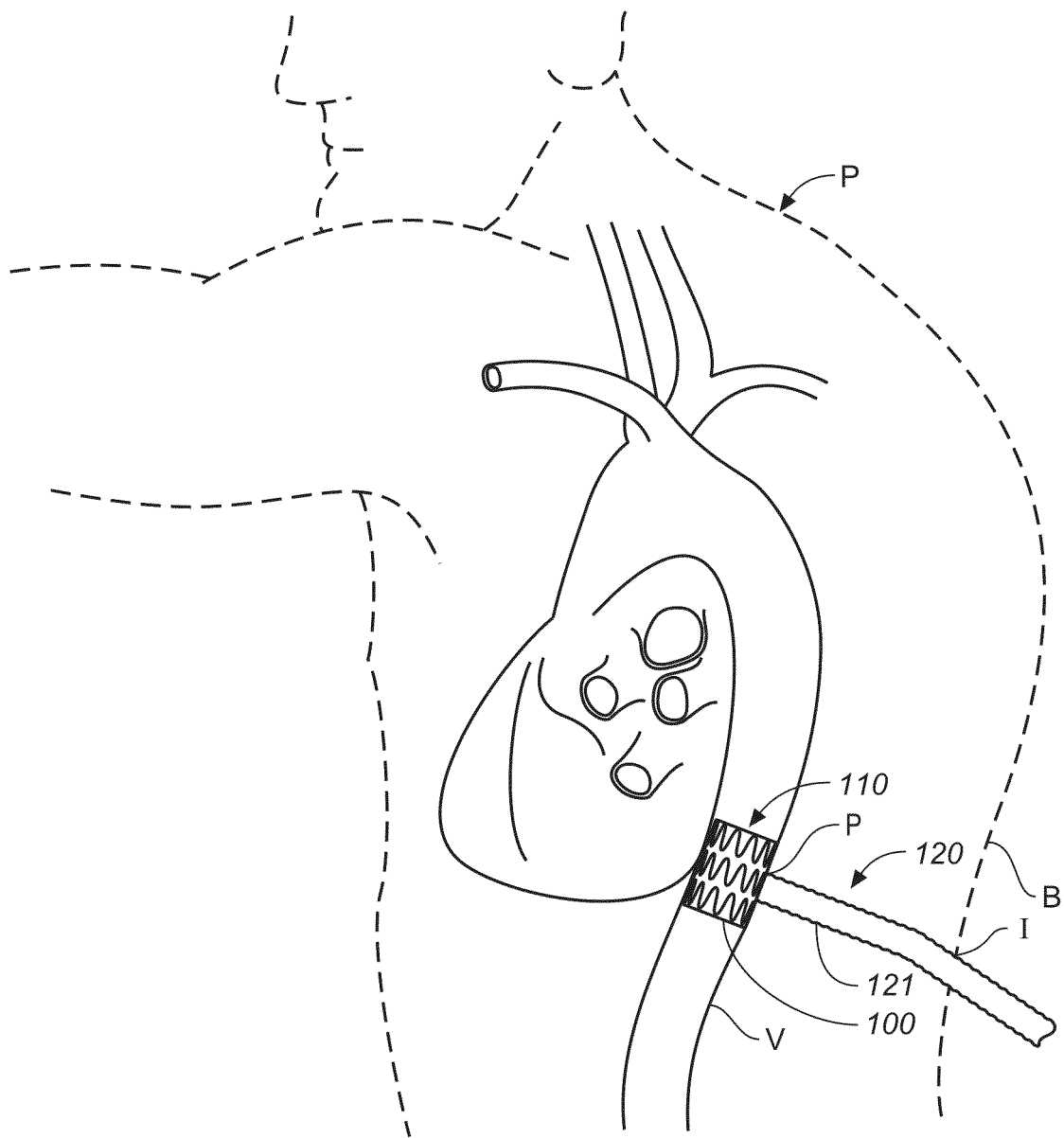
FIG. 6 illustrates a first use of the endovascular stent-graft.

FIG. 6 illustrates the first use to allow external access to a patient P having a back B and an artery (for example aorta or vena cava). Also shown is the site of an incision, I, in the skin of the patient's back and the puncture, P, in the target blood vessel V. Once endovascular stent-graft 100 or 300 is in place in target blood vessel V, the second end 124 of vascular graft 120 is left open and external to the patient. The surgeon then inserts devices for providing minimally invasive surgery, as are known in the art, into second end 124, through the aorta or vein, and to the heart. Once the heart valve is repaired and the device for effecting the repair are removed from endovascular stent-graft 100 or 300, vascular graft 120 is tied off and incision I is sutured. This method has the advantage over the prior art in that the surgeon minimally invasively enters the patent through their back.

If length Lg of vascular graft 120 is not sufficient for the intended use of endovascular stent-graft 100 or 300, then an extension of additional length of graft may be sutured to second end 124, effectively increasing the length of lumen of the vascular graft.

A method to provide the accesses illustrated in FIG. 6 is as follows.

Step 1: A surgeon makes an incision in the patient's skin and directs a needle to the location in the target blood vessel where endovascular stent-graft 100 or 300 is to be delivered and punctures the target blood vessel with the needle. In certain embodiments, the patient is placed on their abdomen and the first incision is made through the patient's back using a trans-lumbar approach.

Step 2: The surgeon inserts a guide wire through the needle and into the target blood vessel, and then removes needle leaving the guide wire in place.

Step 3: The dilator and sheath of the delivery system are passed together over the guide wire, and into the blood vessel, where the tapered tip of the dilator acts to stretch the opening in the blood vessel to allow for the insertion of the larger sheath.

Step 4: Endovascular stent-graft 100 or 300 is provided into a delivery system. Stent-graft 110 is generally similar to conventional stent-grafts and may utilize conventional stent-graft delivery systems. One example of a stent-graft delivery system is, without limitation, a Valiant Thoracic Stent-graft with the Captivia Delivery System (https://www.medtronic.com/us-en/healthcare-professionals/products/cardiovascular/aortic-stent-grafts/valiant-thoracic-stent-graft-with-captivia-delivery-system.html), manufactured by Medtronic (Fridley, Minnesota). Thus, for example and without limitation, stent-graft 110 is compressed and provided into the tip of the delivery system (not shown) with vascular graft 120 extending away from the tip with second end 124 distal to the tip.

Step 5: The surgeon threads the guide wire into the tip of the delivery system, entering compressed endovascular stent-graft 100 or 300 at first end 112 of stent-graft 110, and threading the guide wire through vascular graft 120 to exit the endovascular stent-graft at second end 124

Step 6: The surgeon threads guides the tip of the delivery system, with or without the aid of a computerized tomography (CT) scan, through the sheath and into the target blood vessel.

Step 7: With the compressed stent-graft 110 inside the target blood vessel, and with vascular graft 120 or an extension to the vascular graft extending through the blood vessel puncture and outside of the target blood vessel, the surgeon operates the delivery system to release stent-graft 110, and then removes the delivery system, dilator, guide wire, and sheath, leaving only stent-graft 110 inside the target blood vessel and vascular graft 120 extending through the puncture of the blood vessel and out of the blood vessel.

Step 8: With endovascular stent-graft 100 or 300 so deployed and with vascular graft 120 extending out of the body, the surgeon has access to the blood vessel, and may for example and without limitation, access the heart as required for further treatment.

Figure 5A:
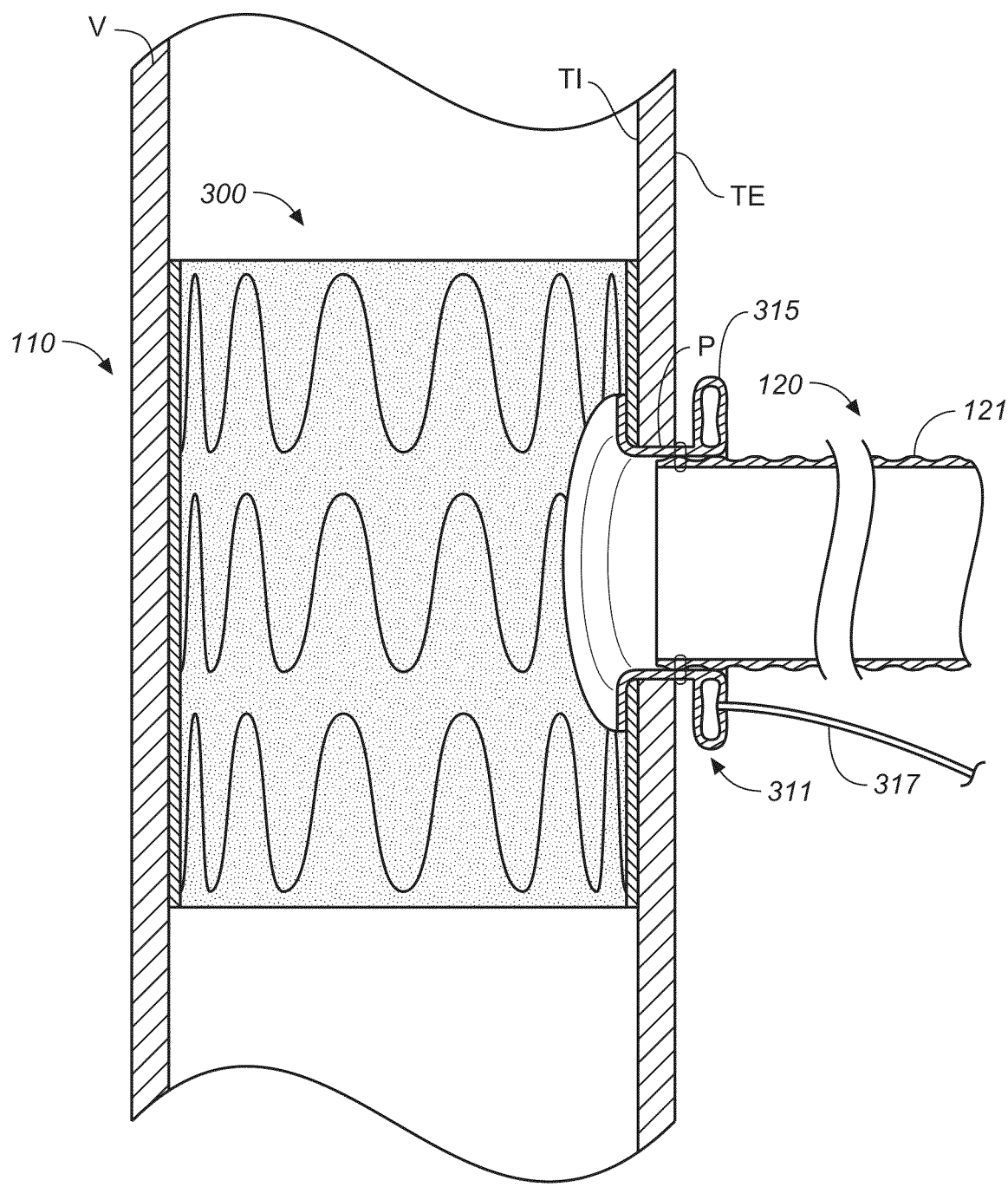
FIGS. 5A and 5B are a first and second side view, respectively, illustrating the placement of the second embodiment endovascular stent-graft in a target blood vessel.
Figure 5B:
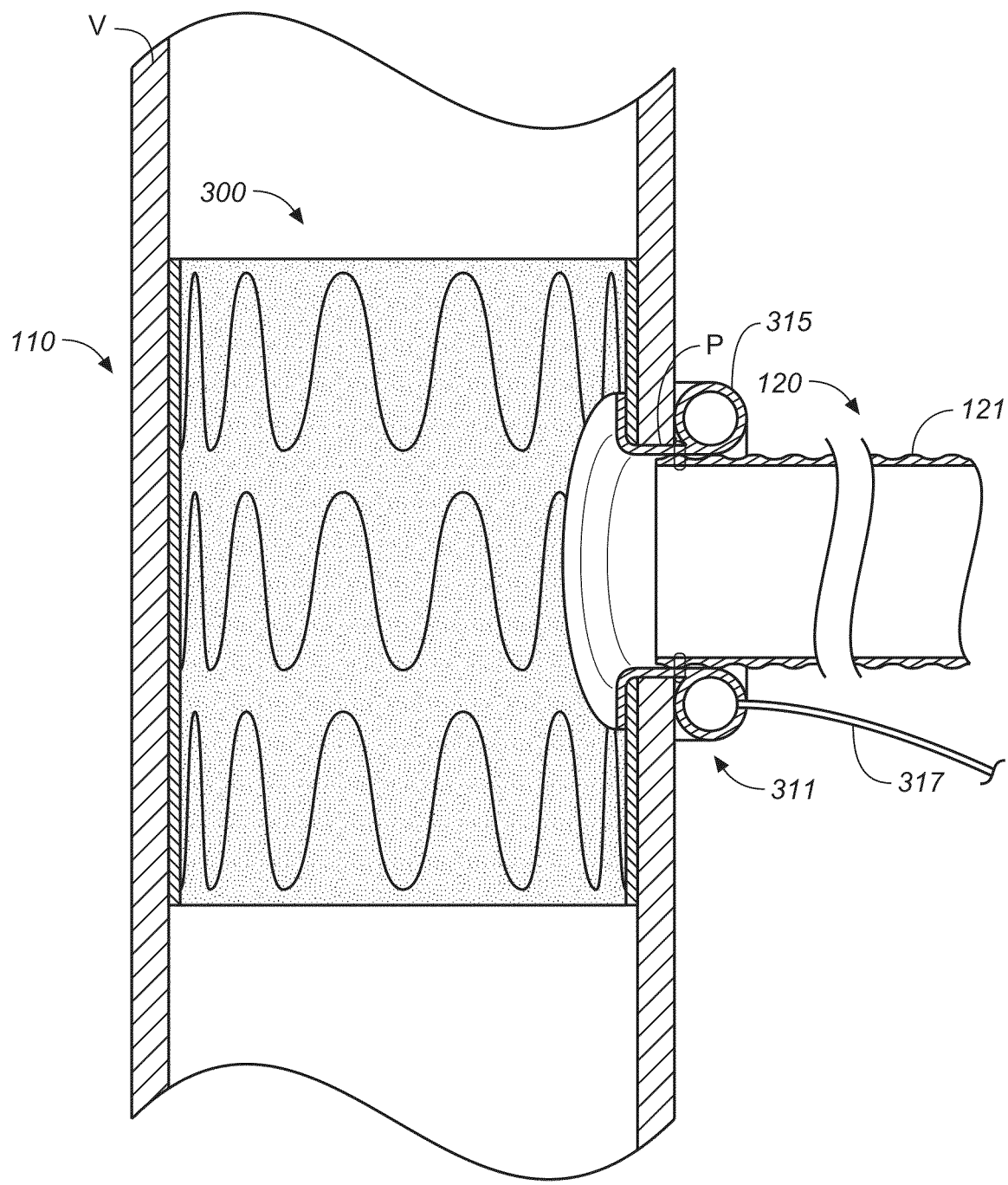

Placing endovascular stent-graft with an extravascular extension 300 requires an extra step, as illustrated for example in FIGS. 5A and 5B, which are a first and second side view, respectively, illustrating the placement of the endovascular stent-graft 300 in a target blood vessel, V.

FIG. 5A illustrates the initial placement of endovascular stent-graft 100, at Step 6, in a target blood vessel, V, having a tunica intima, TI, and tunica externa, TE. The expanded stent-graft 110 contacts tunica intima, TI with vascular graft 120 extending though a puncture P of target blood vessel, V. This figure also illustrates the placement of an expanded endovascular stent-graft 100 in target blood vessel, V.

Next, in Step 7A follows Step 7 as illustrated in FIG. 5B, tube 317 is used to inflate balloon 315. A portion of balloon 315 expands towards and provides a force against tunica externa, TE, compressing target blood vessel, V, between the balloon and stent-graft 110. The resulting compression force acts to secure endovascular stent-graft 300 to the target blood vessel, V, and reduce the likelihood of a leak of blood from the target blood vessel.

A second use of endovascular stent-graft 100 or 300 or dual endovascular stent-graft 700 or 800 is to perform a bypass by connecting two blood vessel locations. Thus, for example, stent-graft 110 of endovascular stent-graft 100 or 300 is deployed through a first puncture in a first blood vessel with vascular graft 120 protruding from the blood vessel, as described above in Steps 1 through 7 or 7A, followed by attaching second end 124 at a second puncture in the same or different blood vessel using well known techniques, such as with an anastomosis between the sent-graft and blood vessel, as used in traditional bypass procedure. The skin incision is then sutured so that endovascular stent-graft 100 or 300 is subcutaneous.

Another example of this second use is to form dual endovascular stent-graft 700 or 800 within the patient. Thus, for example and without limitation, first stent-graft 110A of a first endovascular stent-graft 100 or 300 is deployed through a first puncture of a blood vessel and second stent-graft 110B of a second endovascular stent-graft 100 or 300 is deployed through a second puncture of a blood vessel, where the deployment of both the first and second endovascular stent-grafts is described above in Steps 1 through 7 or 7A. Next first vascular graft 120A and second vascular graft 120B are treaded subcutaneously towards a third skin incision located where first end 124A and second end 124B are to be joined. The ends are then joined to each other forming dual endovascular stent-graft 700 or are joined via an intervening tube 810, forming dual endovascular stent-graft 800. Lastly, the third skin incision is sutured to provide subcutaneous dual endovascular stent-graft 700 or dual endovascular stent-graft 800.

Examples of the second use of endovascular stent-graft 100 or 300 or dual endovascular stent-graft 700 or 800 to perform a bypass includes, but it not limited to: a carotid-carotid bypass; a carotid-subclavian bypass; a carotid-axillary bypass; an axillo-femoral bypass; an aortofemoral bypass; an iliac-femoral bypass; an iliac-popliteal bypass; an femoral-popliteal bypass; an aorta-vena cava arteriovenous graft; an iliac-iliac arteriovenous graft; or a vena cava-femoral arteriovenous graft.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

I claim:

1. A method of performing a procedure on a patient having a first blood vessel including a first lumen having a first lumen inner surface and a second blood vessel including a second lumen with a second lumen inner surface, said method comprising:

incising a skin of the patient to form a first incision, where the first incision is positioned to provide access to a first location of the first blood vessel;

incising a skin of the patient to form a second incision, where the second a incision is positioned to provide access to a second location of the second blood vessel;

puncturing the first blood vessel at the first location to form a first puncture;

puncturing the second vessel blood at the second location to form a second puncture;

providing a first stent-graft of a first endovascular stent-graft through the first incision and the first puncture to contact the first lumen inner surface, where the first endovascular stent-graft includes a branching first vascular graft having a first vascular graft end;

providing a second stent-graft of a second endovascular stent-graft through the second incision and the second puncture to contact the second lumen inner surface, where the second endovascular stent-graft includes a branching second vascular graft having a second vascular graft end;

subcutaneously threading the first vascular graft end towards the second vascular graft end;

connecting the first vascular graft end to the second vascular graft end;

closing the first incision; and closing the second incision, such that the first endovascular stent-graft and second endovascular stent-graft are below the skin of the patient and such that fluid communication is provided between the first blood vessel at the first puncture and the second blood vessel at the second puncture.

2. The method of claim 1, where said connecting the first vascular graft end to the second vascular graft end includes joining the first vascular graft end to the second vascular graft end or connecting the first vascular graft end to the second vascular graft end with an intervening tube.

3. The method of claim 1, further comprising:

incising the skin to form a third incision;

connecting the first vascular graft end to the second vascular graft end through the third incision; and closing the third incision.

4. The method of claim 1, where said first incision is in a patient's back.

5. The method of claim 1, where said procedure is a bypass.

6. The method of claim 5, where said bypass is a carotid-subclavian bypass, a carotid-axillary bypass, an axillo-femoral bypass, an aortofemoral bypass, an iliac-femoral bypass, an iliac-popliteal bypass, an femoral-popliteal bypass, an aorta-vena cava graft, an iliac-iliac arteriovenous graft, or a vena cava-femoral arteriovenous graft.

\* \* \* \* \*